(12) United States Patent
Scholz et al.

(10) Patent No.: US 11,060,068 B2
(45) Date of Patent: Jul. 13, 2021

(54) STABILISATION METHOD FOR VIRUSES OR BACTERIA

(75) Inventors: Martin Scholz, Oberursel (DE); Jens Altrichter, Kavelstorf (DE); Kristina Kemter, Garching bei Munchen (DE)

(73) Assignee: Leukocare AG, Martinsried/Munich (DE)

( * ) Notice: Subject to any disclaimer, the term of this patent is extended or adjusted under 35 U.S.C. 154(b) by 0 days.

(21) Appl. No.: 14/129,057

(22) PCT Filed: Jun. 28, 2012

(86) PCT No.: PCT/EP2012/062630
§ 371 (c)(1),
(2), (4) Date: Dec. 23, 2013

(87) PCT Pub. No.: WO2013/001034
PCT Pub. Date: Jan. 3, 2013

(65) Prior Publication Data
US 2014/0134699 A1    May 15, 2014

(30) Foreign Application Priority Data

Jun. 28, 2011 (EP) .................................... 11005281
Nov. 14, 2011 (EP) .................................... 11009018

(51) Int. Cl.
*C12N 7/00* (2006.01)
*C12N 1/20* (2006.01)

(52) U.S. Cl.
CPC .................. *C12N 7/00* (2013.01); *C12N 1/20* (2013.01); *C12N 2710/10351* (2013.01);
(Continued)

(58) Field of Classification Search
None
See application file for complete search history.

(56) References Cited

U.S. PATENT DOCUMENTS

| 4,537,769 A | * | 8/1985 | Cerini | ................... A61K 38/47 424/209.1 |
| 2006/0228369 A1 | * | 10/2006 | Chen | ..................... A61K 39/39 424/184.1 |

(Continued)

FOREIGN PATENT DOCUMENTS

| EP | 0 090 886 A2 | 10/1983 |
| EP | 2 119 451 A1 | 11/2009 |

(Continued)

OTHER PUBLICATIONS

Wachecketal., "A Novel Type of Influenza Vaccine: Safety and Immunogenicity of Replication-Deficient Influenza Virus Created by Deletion of the Interferon Antagonist NS1," The Journal of Infectious Diseases 201:354-62 (Year: 2010).*

(Continued)

*Primary Examiner* — M Franco G Salvoza
(74) *Attorney, Agent, or Firm* — Gavrilovich, Dodd & Lindsey LLP

(57) ABSTRACT

The present invention relates to a method for stabilising viruses or bacteria, the method comprising embedding the viruses or bacteria in an aqueous solution, wherein the solution comprises: (i) at least three different amino acids; or (ii) at least one dipeptide or tripeptide and wherein the solution is free or substantially free of sugar(s), silanes and protein(s).

18 Claims, 7 Drawing Sheets

Figure 1:
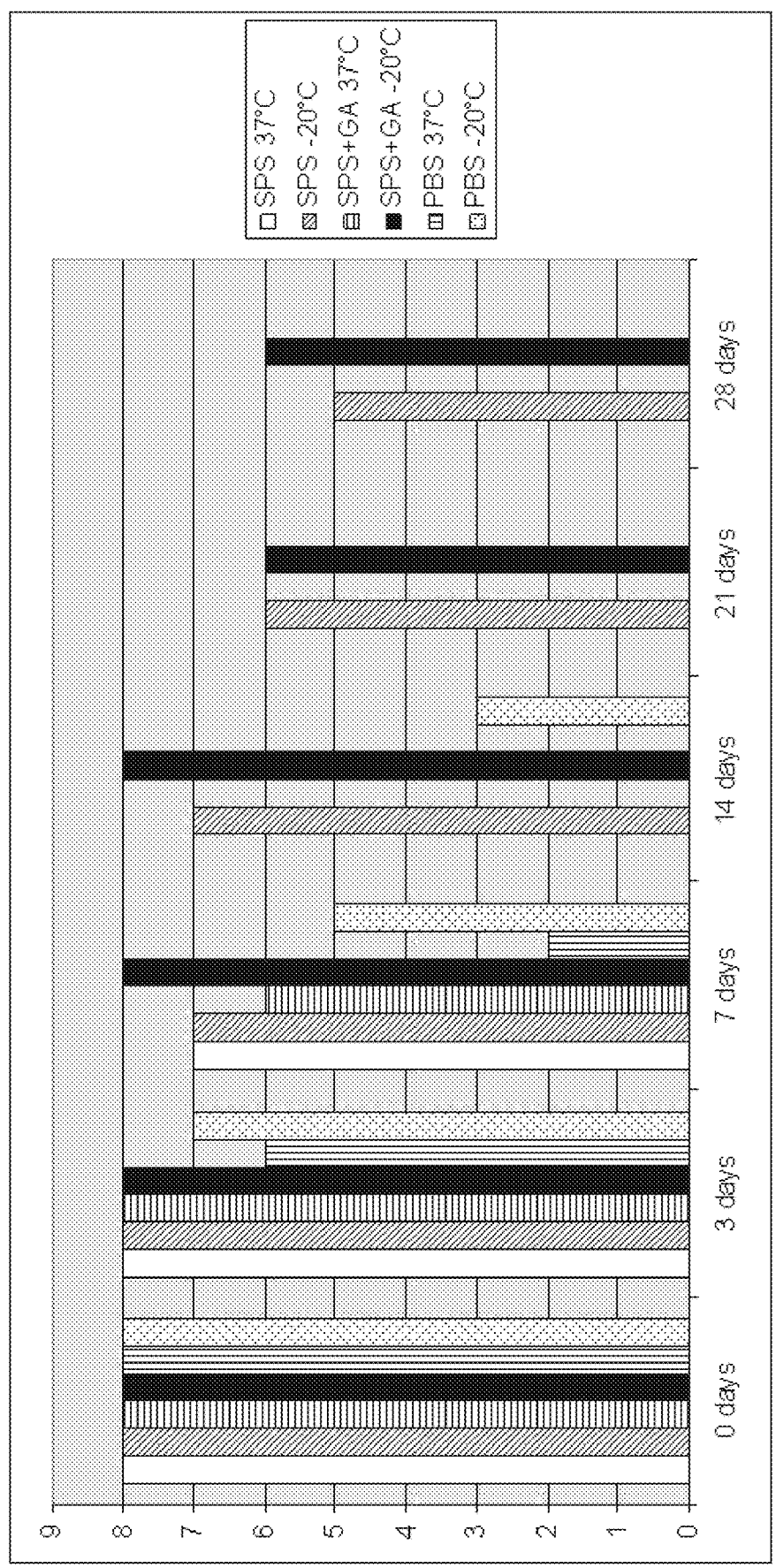

(52) U.S. Cl.
CPC .............. *C12N 2710/16651* (2013.01); *C12N 2760/16051* (2013.01); *C12N 2760/16151* (2013.01)

(56) References Cited

U.S. PATENT DOCUMENTS

| | | | | |
|---|---|---|---|---|
| 2007/0099855 | A1* | 5/2007 | Cinatl | A61K 31/04 514/33 |
| 2008/0003657 | A1* | 1/2008 | Dietzschold | C07K 14/005 435/235.1 |
| 2008/0254065 | A1* | 10/2008 | Podda | A61K 39/145 424/206.1 |
| 2010/0226939 | A1* | 9/2010 | Truong-Le | A61K 39/15 424/215.1 |
| 2011/0081380 | A1* | 4/2011 | Francon | A61K 39/12 424/224.1 |
| 2011/0129494 | A1* | 6/2011 | Detraz | A61K 39/00 424/204.1 |
| 2012/0107829 | A1* | 5/2012 | Margraf et al. | 435/7.1 |
| 2013/0122045 | A1* | 5/2013 | Hirst | A61K 39/145 424/209.1 |

FOREIGN PATENT DOCUMENTS

| | | |
|---|---|---|
| JP | 4-506973 | 12/1992 |
| JP | 6-65096 A | 3/1994 |
| JP | 2008-525444 | 7/2008 |
| JP | 2009-516519 A | 4/2009 |
| JP | 2014-517718 A | 7/2014 |
| WO | 90/05548 A1 | 5/1990 |
| WO | 91/02543 | 3/1991 |
| WO | 2006071373 A1 | 7/2006 |
| WO | 2007/056847 A1 | 5/2007 |
| WO | 2007/110356 A1 | 10/2007 |
| WO | 2009/014774 A1 | 1/2009 |
| WO | 2010/115835 A2 | 10/2010 |

OTHER PUBLICATIONS

Lehninger, "Table 3-1" excerpted from Chapter 3, Principles of Biochemistry, Macmillan (Year: 2005).*
Hubalek Zdenek, "Protectants used in the cryopreservation of microorganisms," Cryobiology, vol. 46, No. 3, pp. 205-229, Jun. 1, 2003.
Didenot, Nathalie, International Search Report, PCT/EP2012/062630, European Patent Office, dated Oct. 17, 2012.
Hamada, Mitsuhiro, Patent Application No. 2014-517718, Appeal No. 2017-002901, Japanese Patent Office, May 12, 2017.
Brouns, Gary, Office Action, EP 12733060.3, European Patent Office, dated Oct. 5, 2016.
Pohjanpelto, Pirkko, "Stabilization of Poliovirus by Cystine," Virology, 6, 472-487 (1958).
Miyaoka, Mai, Office Action, Japanese Patent Office, Application No. 2017-036293, dated Jan. 5, 2018.
Brouns, Gaby, Summons to Attend Oral Proceedings Pursuant to Rule 115(1) EPC, European Patent Office, Application No. 12733060.3, Jul. 5, 2019.
Office Action, Japanese Patent Office Action, dated Mar. 12, 2020, Application No. 2017-036293.
Anonymous: "Product Success Depends on Formulation. Interview with Michael Scholl, CEO of Leukocare", GEN Genetic Engineering and Biotechnology News, Mar. 1, 2017.
Brouns, Gaby, Extended European Search Report, European Patent Office, Application No. 20168140.0, dated Oct. 29, 2020.
Office Action, China National Intellectual Property Administration, Application No. 201810324772.9, dated Feb. 2, 2021.
Yulin, Wang et al., "Screening Studies on Freezing—Drying Stabilizers for Live Viral Vaccines", Progress in Microbiology and Immunology, 1996, pp. 22-27.

* cited by examiner

STABILISATION METHOD FOR VIRUSES OR BACTERIA

CROSS REFERENCE TO RELATED APPLICATIONS

This application is a U.S. National Stage Application filed under 35 U.S.C. § 371 based upon International Application No. PCT/EP2012/062630, filed 28 Jun. 2012, which claims priority to EP11005281.8, filed Jun. 28, 2011, and EP11009018.0, filed Nov. 14, 2011, the disclosures of which are incorporated herein by reference.

The present invention relates to a method for stabilising viruses or bacteria, the method comprising embedding the viruses or bacteria in an aqueous solution, wherein the solution comprises: (i) at least three different amino acids; or (ii) at least one dipeptide or tripeptide and wherein the solution is free or substantially free of sugar(s), silanes and protein(s).

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

All viruses have in common that they require host cells for replication. Therefore, viruses have to infect cells or bacteria where they immediately start the replication machinery of the host cell or remain silent for an undefined period of time. In order to infect host cells, viruses have evolved mechanisms to adhere to cell membranes, where molecules within the viral envelop or capsid interact with specific molecules of the host cell membrane as a prerequisite for the subsequent invasion step. During this step the viruses may use different strategies. For example, the envelope of the virus in the case of enveloped RNA and DNA viruses fuse to form virus genome containing subcellular compartments. The viral genome is then released into the host cell, where—e.g. in the case of DNA viruses such as herpes viruses—the viral DNA may be incorporated into the host cell DNA. When the genome consists of genomic RNA, as it is the case for example for poliovirus, the RNA is directly translated for synthesis of virus specific proteins and a viral polymerase. There are several well described cell invasion mechanisms and replication mechanisms that are used for the classification of viruses. In addition, the virus synthesis steps and the mechanisms involved in the release of viruses (e.g. cytolysis) from the host cell differ between the virus types.

Both host cell invasion and replication depends on molecular interactions between virus and host cells. During the adhesion process, adhesion molecules on the virus envelop may e.g. interact with the respective counterpart on the host cell membrane by tight binding. For example, molecules of rhinovirus can bind to the intercellular adhesion molecule-1 on the host cell membrane. In the case of influenza A, the viral molecules neuraminidase and hemagglutinin are important for the host cell membrane interaction and unpacking of the viral genome.

In other words, viruses carry a large number of molecules that enable both infection and replication in a complex sequence of biomolecular reactions. Consequently, these reactions are insufficient when single molecular reactions do not occur or do not occur correctly. Generally, viruses are very instable under non-physiological conditions, e.g. ex vivo. Physical conditions such as high temperature, dry conditions or irradiation usually lead to virus inactivation, whereas enveloped viruses generally are more sensitive to those conditions than non-enveloped viruses.

Viruses have evolved immune escape mechanisms to avoid being killed by the host immune system after successful host cell infection and replication. Similarly, also the immune system has evolved mechanisms to recognise viruses or virus-infected cells. An important role is the presentation of viral antigenic peptides on the surface membrane of antigen presenting cells such as dendritic cells or monocytes/macrophages via the major histocompatibility complex (MHC) system. For many viruses, the molecules with antigenic potential have been identified and are used for the development of vaccines. These antigens are processed by antigen presenting cells of the host to be presented together with MHC molecules on the surface. Immune cells such as CD4 and CD8 lymphocytes recognise the presented viral peptides and with support of co-stimulatory molecules on the surface membrane of the antigen presenting cells the virus specific lymphocytes expand to form a defence line against the viruses. Consequently, the viral antigens relevant for the development of vaccines have to be in a native condition in order to elicit a potent immune response in the host.

Alternatively, genetically modified organisms (GMOs) such as viral vectors carrying vaccine relevant genes have been developed. For example, adenovirus, cytomegalovirus, vaccinia virus are used for transfection of cells and for immune therapy. Viral vectors may carry genes that encode for proteins that have high potential as antiviral or antioncogenic vaccines. The GMOs used for vaccination ought to have maintained their infectivity in vitro and vivo and have to allow the protein biosynthesis of the transfected genes to trigger a target specific protein expression and immune response.

Essential aspects to be taken into consideration in the development and production of vaccines are (Morefield G L, A rationale approach for the development of vaccine formulations, AAPS Journal, 2011; DOI: 10.1208/s12248-011-9261-1): (1) correct conditions for the propagation of viruses in vitro as well as their storage in order to avoid loss of infectivity and replication, mechanical damage or physical damage). In this regard it is desired to produce large numbers of viruses with high stability, infectivity, replication, and antigenicity. (2) Inactivation steps (i.e. attenuation) are important for safety reasons but have the drawback of increasing the likelihood of modification of the antigen, thus leading to loss of antigenicity. (3) Storage conditions ought to allow recovery of large numbers of viruses. (4) Safety and efficacy of the virus vaccine has to be ensured when formulating the vaccine using suitable adjuvants and stabilizers. (5) The production of the vaccine should be as economical as possible.

US 2011/0081380 describes a vaccine composition comprising an inactivated whole virus and a complex stabilizing excipient which comprises a large number of ingredients, including a buffer solution, a mixture of essential and nonessential amino acids, a disaccharide, a polyol, a chelating agent, urea or an urea derivative and a non-ionic surfactant. This composition is described as advantageous, as it replaces prior art excipients that contain products of animal origin, such as proteins, in order to reduce possible biological safety issues and/or the risk of allergies associated with the use of such products.

EP 2 119 451 A1 describes freeze-dried preparations of influenza vaccines in which the vaccine is stabilized. As is shown in the Examples of EP 2 119 451 A1, activity of an influenza HA vaccine could be maintained in a freeze-dried preparation under specific conditions of pH and ratios of components. Also EP 0 090 886 A2 shows a stabilizing effect of protein hydrolysates, amino acids and combinations thereof on a viral vaccine component, namely neuraminidase. However, both EP 2 119 451 A1 and EP 0 090 886 A2 are focused on the stabilization of a viral component (i.e. the influence HA vaccine or neuraminidase) and not on the stabilization of whole viruses for maintaining their infectivity, ability to replicate and/or antigenicity.

WO 2010/115835 describes a composition comprising amino acids or dipeptides/tripeptide for stabilizing biomolecules immobilized on a solid carrier, wherein the biomolecules can be, amongst others, molecules comprised in or on structures such as cells, tissues, viruses as well as fragments thereof (e.g. organelles, membranes or capsids). Further, international application WO 2010/112576 describes a closed sterilized container comprising a carrier which is a stabilizer and at least one biomolecule reversibly attached to the carrier. The biomolecules can be, e.g., molecules comprised in or on structures such as cells, tissues, viruses as well as fragments thereof. However, the stabilization of whole viruses or bacteria, and in particular the maintenance of their viability and biological activity such as reproduction, infectivity and antigenicity has not been envisioned in these applications.

WO 2009/059784 describes a method of producing a solid coated carrier carrying biological material, wherein the biological material is coupled to the carrier via a silane or a similarly suitable coupler. Thus, the biological material is embedded into a protective matrix on the carrier, which is for use e.g. in therapy, such as the detoxification of body fluids, or for diagnosis, such as e.g. the detection of toxins or specific cell populations in body fluids. The therapeutic or diagnostic effect is achieved without releasing the attached biological material into the body fluid due to the fixation of the biological material on the solid carrier, thus minimizing pharmacokinetic problems caused by circulating active biological material.

Despite the fact that a lot of research is invested into providing suitable methods for the storage of viruses and bacteria, there are significant disadvantages associated with methods known in the art, such as e.g. that they involve the use of animal-derived substances or poorly defined components, require difficult preparation steps, are cost intensive and, most importantly, do not maintain the desired characteristics of the viruses or bacteria. Therefore, there is still a need to provide preparations for the storage of such organisms, for use e.g. in immunological formulations and vaccines, that can be stored for prolonged periods of time and under various stress conditions, without a loss of viability and/or the organisms capability to replicate and/or the organisms infectious potential.

This need is addressed by the provision of the embodiments characterised in the claims.

Accordingly, the present invention relates to a method for stabilising viruses or bacteria, the method comprising embedding the viruses or bacteria in an aqueous solution, wherein the solution comprises: (i) at least three different amino acids; or (ii) at least one dipeptide or tripeptide and wherein the solution is free or substantially free of sugar(s), silanes and protein(s).

The term "viruses" as used herein refers to small infectious agents that can replicate only inside the living cells of organisms. Viruses infect all types of organisms, from animals and plants to bacteria and archaea. Virus particles vary in shape and size, from 0.02 to 0.3 μm and contain RNA or DNA, either double or single stranded, which forms the viral genome. The viruses have a varied structure but the nucleic acid is always located within the virus particle surrounded by a protein coat (capsid or shell). The complex of nucleic acid and protein (the nucleocapsid) may be the whole structure of the viruses (for example φ6, a RNA bacterial virus, or φ174, a DNA bacterial virus) but structures that are more complicated do also occur. The enveloped viruses may have lipid and protein membranes around the capsid while the complex viruses possess not only icosahedral heads but also helical tails with up to 20 proteins within the tail. Non-limiting examples of viruses include influenza viruses, polio viruses, and adenoviruses, arboviruses, astroviruses, bacteriophages, enteroviruses, gastroenteritis viruses, hantaviruses, coxsackie viruses, hepatitis A viruses, hepatitis B viruses, hepatitis C viruses, herpesviruses (for example, Epstein Barr viruses (EBV), cytomegaloviruses (CMV) and herpes simplex viruses (HSV)), norwalk viruses, chordopoxyiridae (i.e., 5 orthopoxviruses, vaccinia, MVA, NYVAC, avipoxviruses, canarypox, ALVAC, ALVAC(2), fowlpox, rhabdoviruses, reoviruses, rhinoviruses, rotaviruses, retroviruses, baculoviridae, caliciviridae, caulimoviridae, coronaviridae, filoviridae, flaviviridae, hepadnaviridae, nodaviridae, orthomyxoviridae, paramyxoviridae, papovaviridae, parvoviridae, phycodnaviridae, picornaviridae, and togaviridae, and modified viruses originating therefrom. Other suitable viruses are known in the art as described in, for example, Fields et al., Virology (34th ed., Lippincott Williams & Wilkins (2001)).

As used herein, the term "bacteria" relates to prokaryotic cells that are generally only a few micrometers in length, and have a wide range of shapes, including e.g. spheres, rods and spirals. Some bacterial species exist as single cells, others associate in characteristic patterns: *Neisseria* for example form diploids (pairs), *Streptococcus* form chains, and *Staphylococcus* group together in clusters. Bacteria can also be elongated to form filaments, for example the *Actinobacteria*. Filamentous bacteria are often surrounded by a sheath that contains many individual cells. Bacteria are often characterised as either gram-positive or gram-negative bacteria and most bacteria can be classified as belonging to one of four groups: gram-positive cocci, gram-positive bacilli, gram-negative cocci and gram-negative bacilli. Non-limiting examples of bacteria include *Escherichia* sp., *Klebsiella* sp., *Salmonella* sp., *Bacillus* sp., *Streptomyces* sp., *Streptococcus* sp., *Shigella* sp., *Staphylococcus* sp., and *Pseudomonas* sp. Non-limiting examples of species within these genuses that include *Escherichia coli, Klebsiella pneumoniae, Bacillus subtilis, Salmonella typhimuritum, Streptomyces aureus, Streptococcus mutans, Streptococcus pneumoniae*, and *Pseudomonas syringae*.

The terms viruses and bacteria are also referred to herein as "organisms of the invention".

In accordance with the present invention, the term "stabilising", relates to the maintenance of the biological activity of the organisms of the invention. This protection of the viruses or bacteria is particularly relevant during storage, such as e.g. when freezing or drying the organisms of the invention. The organisms of the invention is considered to have maintained its "biological activity" when it has the same or essentially the same activity after embedding in a solution in accordance with the invention as the naturally occurring activity of said organisms. Biological activities depend on the specific viruses or bacteria employed and include, for example, the capability to replicate and/or their infectious abilities and/or their antigenicity. The term "essentially the same biological activity" refers to a biological activity of the organisms that is at least 75%, more preferably at least 85% and most preferably at least 95% of the naturally occurring biological activity of said organisms. More preferably, the biological activity of the organisms is at least 98%, more preferably 100% of the naturally occurring biological activity of said organisms. Means to test whether an organism is stabilised are well known to the skilled person and include, without being limiting, testing the infectious potential of viruses (infectivity); the growth of viruses or bacteria (i.e. replication rate) in culture or their antigenicity. Exemplary methods are shown in the appended examples.

The term "embedding", as used herein, relates to the insertion of the organisms in accordance with the invention into the recited solution. Preferably, the material is fully embedded into the solution.

The term "aqueous solution", as used herein, is well known to the person skilled in the art and relates to a solution in which the solvent is water.

The term "amino acid", in accordance with the present invention, relates to organic molecules that have a carboxylic acid group, an amino group and a side-chain that varies between different amino acids. Amino acids are the essential building blocks of proteins. In accordance with the present invention, the term "amino acid" refers to free amino acids which are not bound to each other to form oligo- or polymers such as dipeptides, tripeptides, oligopeptides or polypeptides.

The amino acids comprised in the solution of the present invention can be selected from naturally occurring amino acids as well as artificial amino acids or derivatives of these naturally occurring or artificial amino acids.

Naturally occurring amino acids are e.g. the 20 proteinogenic amino acids glycine, proline, arginine, alanine, asparagine, aspartic acid, glutamic acid, glutamine, cysteine, phenylanine, lysine, leucine, isoleucine, histidine, methionine, serine, valine, tyrosine, threonine and tryptophan. Other naturally occurring amino acids are e.g. carnitine, creatine, creatinine, guanidinoacetic acid, ornithine, hydroxyproline, homocysteine, citrulline, hydroxylysine or beta-alanine.

Artificial amino acids are amino acids that have a different side chain length and/or side chain structure and/or have the amine group at a site different from the alpha-C-atom.

Derivates of amino acids include, without being limiting, n-acetyl-tryptophan, phosphonoserine, phosphonothreonine, phosphonotyrosine, melanin, argininosuccinic acid and salts thereof and DOPA.

In connection with the present invention, all the terms also include the salts of the respective amino acids.

In accordance with the present invention, three or more amino acids, which differ from each other, are comprised in the solution. For example, the term "at least three different amino acids" also relates to at least four different amino acids, such as at least five, at least six, at least seven, at least eight, at least nine, at least ten different amino acids or more, such as at least eleven, at least 12, at least 13, at least 14, at least 15, at least 16, at least 17 or at least 18 different amino acids. The term further encompasses exactly three, exactly four, exactly five, exactly six, exactly seven, exactly eight, exactly nine, exactly ten, exactly eleven, exactly 12, exactly 13, exactly 14, exactly 15, exactly 16, exactly 17 or exactly 18 different amino acids. It will be readily understood by a person skilled in the art that when referring to an amino acid herein, more than one molecule of said amino acid are intended. Thus, the recited amount of different amino acids is intended to limit the amount of different types of amino acids, but not the number of molecules of one type of amino acid. Thus, for example the term "three different amino acids", refers to three different types of amino acids, wherein the amount of each individual amino acid is not particularly limited. Preferably, the number of different amino acids does not exceed 18 different amino acids.

The term "dipeptide or tripeptide", as used herein, relates to peptides consisting of two or three amino acids, respectively. Exemplary dipeptides are glycylglutamine (Gly-Gln, giving rise to an enhanced stability as compared to glutamine alone), glycyltyrosine (Gly-Tyr, giving rise to an increased solubility in water as compared to tyrosine alone), alanylglutamine (Ala-Gln, giving rise to an increased solubility in water as compared to glutamine alone) and glycylglycine.

Further non-limiting examples of naturally occurring dipeptides are carnosine (beta-alanyl-L-histidine), N-acetylcarnosine (N-acetyl-(beta-alanyl-L-histidine), anserine (beta-alanyl-N-methyl histidine), homoanserine (N-(4-aminobutyryl)-L-histidine), kyotorphin (L-tyrosyl-L-arginine), balenine (or ophidine) (beta-alanyl-N tau-methyl histidine), glorin (N-propionyl-γ-L-glutamyl-L-ornithine-δ-lac ethyl ester) and barettin (cyclo-[(6-bromo-8-en-tryptophan)-arginine]).

Examples of artificial dipeptides include, without being limiting, aspartame (N-L-a-aspartyl-L-phenylalanine 1-methyl ester) and pseudoproline.

Exemplary tripeptides are glutathione (γ-glutamyl-cysteinyl-glycine) and its analogues ophthalmic acid (L-γ-glutamyl-L-α-aminobutyryl-glycine) as well as norophthalmic acid (γ-glutamyl-alanyl-glycine). Further non-limiting examples of tripeptides include isoleucine-proline-proline (IPP), glypromate (Gly-Pro-Glu), thyrotropin-releasing hormone (TRH, thyroliberin or protirelin) (L-pyroglutamyl-L-histidinyl-L-prolinamide), melanostatin (prolyl-leucyl-glycinamide), leupeptin (N-acetyl-L-leucyl-L-leucyl-L-argininal) and eisenin (pGlu-Gln-Ala-OH). It is preferred that the at least one di- or tripeptide and more preferred all di- or tripeptides, when used in connection with medical applications, do not exert any pharmacological properties.

Preferably, at least one dipeptide is selected from the group consisting of carnosin, glycyltryrosine, glycylglycine and glycylglutamine.

In accordance with the present invention, the solution comprises one or more di- or tripeptides. For example, the term "at least one dipeptide or tripeptide" also relates to at least two di- or tripeptides, such as at least three, at least four, at least five, at least six, at least seven, at least eight or at least nine di- or tripeptides. The term further encompasses exactly one, exactly two, exactly three, exactly four, exactly five, exactly six, exactly seven, exactly eight or exactly nine di- or tripeptides. Where more than one di- or tripeptide is comprised in the solution, a mixture of dipeptides and tripeptides is explicitly envisaged herein. The number of di- and tripeptides can be selected independently of each other, e.g. the solution may comprise two dipeptides and three tripeptides. It will be readily understood by the skilled person that when referring to a certain number of di- and tripeptides herein, said number is intended to limit the amount of different types of di- and tripeptides, but not the number of molecules of one type of dipeptide or tripeptide. Thus, for example the term "four dipeptides or tripeptides", refers to four different types of dipeptides and/or tripeptides, wherein the amount of each individual di- and/or tripeptide is not particularly limited. Preferably, the number of (different) di- or tripeptides does not exceed nine di- or tripeptides.

Preferred amounts of amino acids, dipeptides and/or tripeptides to be employed are between 0.1 and 150 mg/ml, preferably between 1 and 100 mg/ml, more preferably between 10 and 50 mg/ml, even more preferably between 20 and 35 mg/ml and most preferably the amount is 25 mg/ml.

The term "free or substantially free of (a) sugar", in accordance with the present invention, refers to a solution devoid of or substantially devoid of any types of sugars, i.e. the monosaccharide, disaccharide or oligosaccharide forms of carbohydrates as well as sugar alcohols. Examples of sugars commonly used in methods of virus formulations, but absent in accordance with the present invention, include without being limiting saccharose, trehalose, sucrose, glucose, lactose, sorbitol or mannitol. The solution is considered to be substantially free of sugar if it contains less than 0.1% (w/v) sugar, more preferably less than 0.01% (w/v) and even more preferably less than 0.001% (w/v) and most preferably less than 0.0001% (w/v).

The term "free or substantially free of silanes", as used herein, refers to a solution that does not or does not substantially comprise any silane such as for example alkoxysilanes, organofunctional silanes, hydrogensil(ox)anes, siloxanes and organosilanes comprising silyl compounds with other functional groups. The solution is considered to be substantially free of silanes if it contains less than 0.01% (w/v) silanes, more preferably less than 0.001% (w/v) and most preferably less than 0.0001% (w/v).

As used herein, the term "free or substantially free of protein" refers to a solution that does not comprise or does not substantially comprise any proteins other than the proteins naturally associated with the organisms in accordance with the invention. It will be appreciated by the skilled person that trace amounts of proteins associated with e.g. contamination of the solution may be present and are not excluded by the requirement that the solution is free of protein. Thus, the solution is considered to be substantially free of protein if it contains less than 0.1% (w/v) proteins not naturally associated with the organisms to be protected, more preferably less than 0.01% (w/v), even more preferably less than 0.001% (w/v) and most preferably less than 0.0001% (w/v).

In accordance with the present invention, it was surprisingly found that a solution as defined herein stabilises viruses or bacteria during storage. In other words, the material is protected during storage against loss of viability, loss of its capability to reproduce and/or loss of antigenicity. Viral storage media known in the art, such as e.g. the viral transport medium offered by Hardy Diagnostics (Cat. no. R99) or the Universal Transport Medium (UTM-RT) offered by Millipore (Cat. no. 350CM) provide maximum holding times of up to four days. The solution in accordance with the present invention however provides a longer storage time at various temperatures, such as for example at 37° C. or at −20° C. As is shown in Example 1 below, the inventive solution provides protection for as long as 4 weeks, while significant less protection is achieved when viruses are stored in PBS.

The improved stability in particular at increased temperatures such as e.g. 37° C. enables prolonged storage in conditions without refrigeration, such as for example in countries with hot climate and insufficient possibilities of maintaining the required cold chain necessary for state of the art products.

Furthermore, when testing the solution for the storage of eukaryotic cells, it was found that eukaryotic cells suspended in the same solution did not survive freezing and thawing when dimethylsufoximine (DMSO) was completely or partially substituted by the solution of the invention for stabilizing viruses or bacteria. DMSO is known to prevent crystal formation during freezing and drying, thereby reducing the damaging of intracellular structures and cell death. Thus, the finding of the protective effect of the solution in accordance with the invention on viruses and bacteria is even more surprising. Without wishing to be bound by theory, the present inventors speculate that differences in the amount of water and the complexity of the intracellular organelles and structures between eukaryotic cells and viruses and bacteria might explain the lack of a protective effect of the solution in accordance with the present invention when freezing and thawing eukaryotic cells, thus leading to the destruction of these structures inside eukaryotic cells regardless of the extracellular presence of the inventive solution. However, also viruses are known to be extremely sensitive towards physical stress. Especially the titers of enveloped viruses such as HSV-1 generally rapidly decrease after freezing and thawing. Thus, the stabilisation of viral and bacterial infectivity, replication, and antigenicity observed herein represents a surprising finding not expected by the skilled person in the art.

Finally, a further advantage of the inventive solution lies in the lack of additives generally employed in the art, which offers the additional advantage that such additives need not be removed prior to use of the viruses or bacteria and a simplified and less cost-intensive preparation of the stabilising solution.

Preferably, the solution is further free of gelatine and/or phosphate buffer. Most preferably, the method for stabilising viruses or bacteria comprises embedding the viruses or bacteria in an aqueous solution, wherein the solution consists of: (i) at least three different amino acids; or (ii) at least one dipeptide or tripeptide and a saponine or a fatty acid. Even more preferably, the method for stabilising viruses or bacteria comprises embedding the viruses or bacteria in an aqueous solution, wherein the solution consists of: (i) at least three different amino acids; or (ii) at least one dipeptide or tripeptide.

In a further preferred embodiment of the method of the invention, the at least three amino acids are selected from the groups of (a) amino acids with non polar, aliphatic R groups; (b) amino acids with polar, uncharged R groups; (c) amino acids with positively charged R groups; (d) amino acids with negatively charged R groups and (e) amino acids with aromatic R groups.

The naturally occurring amino acids, but also other than naturally occurring amino acids such as artificial amino acids, can be classified into the above characteristic groups (Nelson D. L. & Cox M. M., "Lehninger Biochemie" (2005), pp. 122-127), from which at least three amino acids are selected for the solution according to the invention.

In a more preferred embodiment, the at least three amino acids are selected from different groups (a) to (e). In other words, in this preferred embodiment, when three amino acids are comprised in the solution, the three amino acids may be selected from at least two different groups and, more preferably, from three different groups such that one is from group (a), one is from group (b) and one is from group (c). Further combinations such as e.g. (b)-(c)-(d), (c)-(d)-(e), (e)-(a)-(b), (b)-(d)-(e) and so forth are also explicitly envisaged herein. The same consideration applies when four amino acids are comprised in the solution, in which case the amino acids have to be from at least two different groups selected from (a) to (e), more preferably from at least three different groups and most preferably from four different groups. Inter alia, when five amino acids are comprised in the solution, the amino acids have to be from at least two different groups selected from (a) to (e), more preferably from at least three different groups, more preferably from at least four different groups and most preferably from five different groups. The same considerations apply when more than five amino acids are comprised in the solution, such as e.g. six or seven amino acids, in which case these amino acids are selected from at least two different groups selected from (a) to (e), more preferably from at least three different groups, even more preferably from at least four different groups and most preferably from five different groups.

In an even more preferred embodiment of the method of the invention, the solution comprises at least one amino acid selected from each group of (a) an amino acid with non polar, aliphatic R groups; (b) an amino acid with polar, uncharged R groups; (c) an amino acid with positively charged R groups; (d) an amino acid with negatively charged R groups and (e) an amino acid with aromatic R groups.

The skilled person further understands that it is not necessary that the same number of amino acids of each group is present in the solution used according to the invention. Rather, any combination of amino acids can be chosen as long as at least one amino acids of each group is present.

Furthermore, the amino acids can be present in the solution as singular molecules and/or as di- and/or tripeptides.

In another preferred embodiment of the method of the invention, the solution comprises at least the amino acids: (a) alanine, glutamate, lysine, threonine and tryptophane; (b) aspartate, arginine, phenylalanine, serine and valine; (c) proline, serine, asparagine, aspartate, threonine, phenylalanine; (d) tyrosine, isoleucine, leucine, threonine, valine; or (e) arginine, glycine, histidin, alanine, glutamate, lysine, tryptophane. In another preferred embodiment, the solution comprises at least the amino acids: (f) alanine, arginine, glycine, glutamate, lysine.

In accordance with this embodiment, at least the above recited amino acids of either group (a), (b), (c), (d) or (e) are present in the solution in accordance with the invention. In other words, whereas more than the above recited amino acids may be comprised in the inventive solution, it is required that at least the recited amino acids are present. More preferably, the solution comprises exactly the recited amino acids and no other amino acids. The same consideration apply mutatis mutandis to the amino acids of group (f).

In a further preferred embodiment of the method of the invention, one or more of the amino acids are selected from the group consisting of natural non-proteinogenic amino acids and synthetic amino acids.

The term "non-proteinogenic amino acids", in accordance with the present invention, relates to amino acids that are not naturally incorporated into polypeptides and proteins. Non-proteinogenic amino acids can be derived from proteinogenic amino acids, which are L-α-amino acids, by post-translational modifications. Such non-proteinogenic amino acids are, for example, lanthionine, 2-aminoisobutyric acid, dehydroalanine, and the neurotransmitter gamma-aminobutyric acid. Also the D-enantiomers of proteinogenic L-amino acids represent non-proteinogenic amino acids. Further non-limiting examples of non-proteinogenic amino acids include carnitine, creatine, creatinine, guanidinoacetic acid, ornithine, hydroxyproline, homocysteine, citrulline, hydroxylysine or beta-alanine.

The term "synthetic amino acids", as used herein, relates to amino acids not naturally occurring in nature. Non-limiting examples of synthetic amino acids include (2R)-amino-5-phosphonovaleric acid, D-phenyl glycine or (S)- and (R)-tert-leucine.

In another preferred embodiment of the method of the invention, the solution further comprises an amphiphilic molecule.

The term "amphiphilic molecule", in accordance with the present invention, relates to a molecule possessing both hydrophilic, i.e. water-loving, and lipophilic, i.e. fat-loving, properties. Non-limiting examples of amphiphilic molecules include saponins, fatty acids, phospholipids, cholesterol, glycolipids and bile acids. It is preferred that the amphiphilic molecule used in the stabilising solution, when used in connection with medical applications, does not exert any pharmacological properties.

Saponines are a class of chemical compounds forming secondary metabolites which are found in natural sources, derived from natural sources or can be chemically synthesized. Saponines are found in particular abundance in various plant species. Saponines are amphipathic glycosides grouped phenomenologically by the soap-like foaming they produce when shaken in aqueous solutions, and structurally by their composition of one or more hydrophilic glycoside moieties combined with a lipophilic steroidal or triterpenoid aglycone. Their structural diversity is reflected in their physicochemical and biological properties. Examples of saponines are glycyrrhicic acid, glycyrrhetinic acid, glucuronic acid, escin, hederacoside and digitonin.

Fatty acids are carboxylic acids with a long unbranched aliphatic chain (tail) that may be saturated or unsaturated. They are important energy sources because their metabolism yields large quantities of ATP. The majority of naturally occurring fatty acids have a chain of an even number of carbon atoms, from four to 28 and are usually derived from triglycerides or phospholipids. Fatty acids have different lengths, which is used to categorise them as short-, medium-, or long-chain fatty acids. Short-chain fatty acids (SCFA) are fatty acids with aliphatic tails of fewer than six carbons; medium-chain fatty acids (MCFA) are fatty acids with aliphatic tails of 6-12 carbons, which can form medium-chain triglycerides; long-chain fatty acids (LCFA) are fatty acids with aliphatic tails longer than 12 carbons and very-long-chain fatty acids (VLCFA) are fatty acids with aliphatic tails longer than 22 carbons. Non-limiting examples of fatty acids include unsaturated fatty acids such as e.g. myristoleic acid, palmitoleic acid, sapienic acid, oleic acid, linoleic acid, α-linolenic acid, arachidonic acid, eicosapentaenoic acid, erucic acid and docosahexaenoic acid or saturated fatty acids such as e.g. lauric acid, myristic acid, palmitic acid, stearic acid, arachidic acid, behenic acid, lignoceric acid and cerotic acid.

Phospholipids are a class of lipids that are a major component of all cell membranes as they can form lipid bilayers. The majority of phospholipids contain a diglyceride, a phosphate group, and a simple organic molecule such as choline. One exception is sphingomyelin, which is derived from sphingosine instead of glycerol. Non-limiting examples of phospholipids are phosphatidylcholine (lecithin), phosphatidic acid (phosphatidate), phosphatidylethanolamine (cephalin), phosphatidylserine, phosphatidylinositol, phosphatidylinositol phosphate, phosphatidylinositol bisphosphate, phosphatidylinositol triphosphate, ceramide phosphorylcholine and ceramide phosphorylglycerol.

Cholesterol is a steroid metabolite found in cell membranes and transported in the blood plasma of all animals. It is an essential structural component of mammalian cell membranes, where it is required to establish proper membrane permeability and fluidity. In addition, cholesterol is an important component for the manufacture of bile acids, steroid hormones, and Vitamin D. Cholesterol has the structure:

[Chemical structure of cholesterol]

Glycolipids are lipids with a carbohydrate attached. Their natural role is to provide energy and to serve as markers for cellular recognition. Non-limiting examples of glycolipids include galactolipids, sulfolipids, sulfatides, cerebrosides, galactocerebrosides, glucocerebrosides, glucobicaranateoets, gangliosides, globosides, glycophosphosphingolipids and glycosylphosphatidylinositols.

Bile acids are steroid acids found predominantly in the bile of mammals. The two major bile acids are cholic acid, and chenodeoxycholic acid. Further non-limiting examples of bile acids are glycocholic acid, taurocholic acid, deoxcholic acid and lithocholic acid.

As is shown in the appended examples, the addition of an amphiphilic molecule (e.g. glycyrrhicic acid) to the stabilising solution further improved the virus titer after storage at −20° C. for as long as 4 weeks.

In a more preferred embodiment of the method of the invention, the amphiphilic molecule is selected from the group consisting of a saponine or a fatty acid or derivatives thereof.

In another more preferred embodiment of the method of the invention, the saponine is glycyrrhizic acid or a derivative thereof.

Glycyrrhizic acid is also known as glycyrrhicic acid, glycyrrhizin or glycyrrhizinic acid and has the structure:

[Chemical structure of glycyrrhizic acid]

Glycyrrhizic acid is water-soluble and exists as an anion that can be a potential ligand to form electrostatically associated complexes with cationic molecule active ingredients. Without wishing to be bound by theory, the present inventors hypothesize that the anionic glycyrrhizic acid forms complexes with amino acids present in the solution of the present invention (i.e. arginine, or lysine) through electrostatic interactions, hydrogen bonds or both. This complexation is thought to enhance the ability of the solution of the present invention to stabilize the viruses or bacteria during storage. Moreover, the ability of glycyrrhizic acid to form complexes with cationic molecule active ingredients can lead to interactions with exposed cationic side chains on the protein surface during the storage process.

Derivatives of glycyrrhizic acid are well-known in the art and include those produced by transformation of glycyrrhizic acid on carboxyl and hydroxyl groups, by conjugation of amino acid residues into the carbohydrate part or the introduction of 2-acetamido-β-D-glucopyranosylamine into the glycoside chain of glycyrrhizic acid. Other derivatives are amides of glycyrrhizic acid, conjugates of glycyrrhizic acid with two amino acid residues and a free 30-COOH function and conjugates of at least one residue of amino acid alkyl esters in the carbohydrate part of the glycyrrhizic acid molecule. Examples of specific derivatives can be found e.g. in Kondratenko et al. (Russian Journal of Bioorganic Chemistry, Vol 30(2), (2004), pp. 148-153).

In accordance with the present invention, it was surprisingly found that addition of glycyrrhizic acid to the above described solution further aids in the stabilization of viruses and/or bacteria. Thus, addition of glycyrrhizic acid aids in maintaining the biological activity of viruses and/or bacteria during storage.

In another more preferred embodiment of the method of the invention, the fatty acid is selected from the group consisting of short chain and medium chain fatty acids.

Short chain and medium chain fatty acids are particularly preferred due to their better solubility in water as compared to fatty acids with longer chains.

In another preferred embodiment of the method of the invention, the w/w ratio between the excipients of the solution and the viruses or bacteria is between about 1:1 and about 500:1.

In accordance with this embodiment, the excipients of the solution are the non-aqueous components of the solution that are not the virus or bacteria to be stabilised.

More preferably, the w/w ratio between the components of the solution and the viruses or bacteria is between about 1:1 and about 350:1, such as for example between about 5:1 and about 200:1, or between about 10:1 and about 100:1. Most preferably, the w/w ratio is about 2:1. It will be understood that any value falling between these ratios is explicitly also envisaged herein. Furthermore, the term about, as used herein, encompasses the explicitly recited ratios as well as deviations therefrom of ±10%.

In another preferred embodiment of the method of the invention, the viruses or bacteria maintain their infectivity and/or their ability to replicate.

The term "infectivity", as used herein, relates to the ability of a virus or bacteria to establish an infection in a host or host cell. More specifically, infectivity is the capacity for horizontal transmission of the virus or bacteria, i.e. its spread between hosts rather than from parent to child. Means for determining whether a virus or bacteria has maintained its infectivity are well known in the art and include, without being limiting, testing a cell culture obtained from a host with regard to replication of the virus, PCR analysis, animal models as well as electron-optical analysis. Further methods are provided in the appended examples herein below. A virus or bacterium is considered to have maintained its infectivity in accordance with the present invention when the amount of infectivity is at least 30% of the infectivity of said organism prior to embedding it in the inventive solution. More preferably, the amount of infectivity is at least 50%, more preferably at least 70%, such as at least 95% and most preferably at least 98% of the infectivity of said organism prior to embedding it in the inventive solution.

Viruses and bacteria replicate by copying their genetic material, thus reproducing themselves. Contrary to other organisms, viruses need host cells in order to be able to replicate, as they do not possess their own metabolism. The ability to replicate is maintained if the organisms, subsequently to the method of the present invention, can reproduce itself. Preferably, at least 30% of the organism originally employed in the method of the invention are capable of reproducing subsequent to this method of stabilising said organisms. More preferably, at least 50%, more preferably at least 70%, such as at least 95% and most preferably at least 98% of the organism originally employed in the method of stabilisation of the invention are capable of reproducing subsequent to this method of stabilising said organisms. Most preferably, all of the organism originally employed, i.e. 100%, are capable of reproducing subsequent to this method of stabilising said organisms. Methods to test whether a virus or bacterium has maintained its ability to replicate are well known in the art and include mainly cell culture models with permissive host cells but also PCR analysis, animal experiments, replication in embryonated chicken eggs, electron-optical analysis, hemagglutination tests as well as the determination of virus amounts via plaque titers.

In accordance with the present invention, it has been found that viruses embedded in the solution in accordance with the invention not only survive for a prolonged period of time, but also maintain their infectious capabilities and their ability to reproduce.

In a further preferred embodiment of the method of the invention, the method further comprises the step of subsequently storing the stabilised viruses or bacteria at a temperature selected from about −90° C. to about 45° C. More preferably, the stabilised viruses or bacteria are subsequently stored at a temperature selected from about −90° C. to about −70° C., about −30° C. to about −10° C., about 1° C. to about 10° C. and about 30° C. to about 43° C. Even more preferably, the stabilised viruses or bacteria are subsequently stored at a temperature selected from about −85° C. to about −75° C., about −25° C. to about −150° C., about 2° C. to about 8° C. and about 35° C. to about 40° C. Most preferably, the stabilised viruses or bacteria are subsequently stored at a temperature selected from about −80° C., about −20° C., room temperature, about 4° C. and about 37° C.

It will be appreciated by the skilled person that the term "about", as used herein, encompasses the explicitly recited values as well as small deviations therefrom. In other words, a temperature of "about −90° C." includes but does not have to be exactly the recited amount of −90° C. but may differ by several degrees, thus including for example −91° C., −92° C., −89° C. or −88° C. The skilled person is aware that such values are relative values that do not require a complete accuracy as long as the values approximately correspond to the recited values. Accordingly, a deviation from the recited value of for example 15%, more preferably of 10%, and most preferably of 5% is encompassed by the term "about".

In another preferred embodiment of the method of the invention, the stabilised viruses or bacteria are supplied for storage as a liquid preparation.

In a further preferred embodiment of the method of the invention, the stabilised viruses or are supplied for storage as a dried preparation.

As described herein below, such stored viruses and bacteria (in liquid or dried preparations) may be subsequently used for the preparation of antigen materials.

The term "dried preparation", as used herein, refers to a preparation in which the liquid content has been removed or reduced. Suitable methods for drying a viral or bacterial preparation include, without being limiting, lyophilisation (freeze-drying), spray-drying, freeze-spray drying, air drying or foam drying.

The liquid content is considered to have been reduced if the liquid is reduced to less than 20% of the volume, such as for example less than 10%, such as for example less than 5%, more preferably less than 3% of the volume, such as less than 2% or less than 1%. Most preferably, the liquid is reduced to 0.5% or less.

Lyophilisation, also referred to as freeze-drying, is well known in the art and includes the steps of freezing the organisms and subsequently reducing the surrounding pressure while adding sufficient heat to allow the frozen water in the material to sublime directly from the solid phase to the gas phase. Preferably, the lyophilised preparation is then sealed to prevent the re-absorption of moisture.

Spray-drying is also well known in the art and is a method to convert a solution, suspension or emulsion into a solid powder in one single process step. Generally, a concentrate of the liquid product is pumped to the atomising device, where it is broken into small droplets. These droplets meet a stream of hot air and they loose their moisture very rapidly while still suspended in the drying air. The dry powder is separated from the moist air in cyclones by centrifugal action—the dense powder particles are forced toward the cyclone walls while the lighter, moist air is directed away through the exhaust pipes.

Spray-freeze-drying is also well known in the art and is a method that combines processing steps common to freeze-drying and spray-drying. The organisms provided in the solution according to the invention is nebulized into a cryogenic medium (such as e.g. liquid nitrogen), which generates a dispersion of shock-frozen droplets. This dispersion is then dried in a lyophiliser.

Foam drying is a scalable technology for preservation of sensitive biotherapeutics in the dry state. Therapeutic biomolecules stable at moderate temperatures and pressures, such as erythropoietin, enzymes, and vaccines, are commonly stabilized in the presence of protectants, such as commonly available lyophilizers, using vacuum foam drying (VFD). The suspension or solution of biologicals is transformed into foam by boiling under vacuum, above freezing point, but significantly below 100° C. The foam consists of thin films of material from which water can be efficiently removed at an elevated temperature. The process is based on the principle of evaporation under vacuum at low temperatures.

In accordance with this embodiment, the viruses or bacteria are stabilised in the solution in accordance with the invention and are subsequently subjected to a drying step. The reduced water content inhibits the action of e.g. enzymes that could degrade the organisms and, thus, offers additional protection. Furthermore, surface antigens as well as proteins necessary for host cell binding that are present on the envelope or coat of e.g. a virus or on the cell membrane of bacteria are protected during the drying step, thus maintaining the antigenicity of the viruses or bacteria as well as the interaction with host cells. Thus, after reconstitution, the viruses and bacteria may be employed as live vaccines or as attenuated or killed vaccines via the presentation of surface antigens.

Most preferably, the method of the present invention is not followed by an inactivation step, thus maintaining the viability and replication activity of the organisms of the invention.

However, in an alternative embodiment, and where live vaccines are not required, the method of the present invention may be further followed by an inactivation step. As is shown in the appended examples (see examples 2 and 3), the antigenicity of surface proteins was maintained after inactivation with beta-irradiation (25 kGy) in the presence of the solution according to this invention. Consequently, even though irradiation will result in the loss of replication activity of virus such as e.g. adenovirus and porcine parvovirus, they nonetheless can maintain their antigenicity. Thus, the method of the present invention provides a starting point for the preparation of stable and safe viral or bacterial antigens in the context of vaccine production steps, wherein a virus or bacterium is first stabilised in its natural conformity and then inactivated, while maintaining its naturally occurring three-dimensional appearance. Consequently, and preferably, the context in which antigens are normally presented on the surface of viruses or bacteria remains intact, as no fragmentation of the viruses or bacteria occurs.

It will be appreciated by the skilled person that inactivation is a commonly used term in the art including techniques such as e.g. irradiation, formaldehyde inactivation or β-propiolactone inactivation.

In accordance with the present invention, the viruses may be coated DNA viruses, non-coated DNA viruses, coated RNA viruses and non-coated RNA viruses.

The term "DNA virus", as used herein, refers to a virus that has DNA as its genetic material and replicates using a DNA-dependent DNA polymerase. The nucleic acid is either double-stranded DNA (dsDNA) or single-stranded DNA (ssDNA). DNA viruses belong to either Group I or Group II of the Baltimore classification system for viruses. Non-limiting examples of dsDNA viruses include, Myoviridae such as e.g. Enterobacteria phage T4; Podoviridae; Siphoviridae such as for example Enterobacteria phage λ; Herpesviridae; Adenoviridae; Baculoviridae; Iridoviridae; Papillomaviridae; Polyomaviridae suchg as e.g. Simian virus 40; Poxyiridae such as for example Cowpox virus or smallpox; while non-limiting examples of ssDNA viruses include Inoviridae; Microviridae and Parvoviridae, such as e.g. Parvovirus B19.

As used herein, the term "RNA virus" refers to a virus that has RNA as its genetic material. This nucleic acid may be single-stranded RNA (ssRNA) or double-stranded RNA (dsRNA). RNA viruses classified as those that belong to group III, group IV or group V of the Baltimore classification system of classifying viruses. Non-limiting examples of ssRNA viruses include, Coronaviridae such as e.g. Coronavirus or SARS; Roniviridae; Picornaviridae, such as for example Poliovirus, the common cold virus or Hepatitis A virus; Flaviviridae such as e.g. Yellow fever virus, West Nile virus, Hepatitis C virus, Dengue fever virus; Togaviridae such as e.g. Rubella virus or Ross River virus; Hepevirus such as for example Hepatitis E virus; Tobamovirus including for example tobacco mosaic virus; Bornaviridae including e.g. Borna disease virus; Filoviridae such as for example Ebola virus or Marburg virus; Paramyxoviridae which includes e.g. Measles virus or Mumps virus; Rhabdoviridae, such as e.g. Rabies virus; and Orthomyxoviridae such as for example Influenza viruses; while non-limiting examples of dsRNA viruses include Birnaviridae; Chrysoviridae; Cystoviridae; Hypoviridae; Partitiviridae; Reoviridae such as for example Rotavirus and Totiviridae.

Coated viruses posses an outer protein coat, also called capsid. The capsid surrounds the genetic information of the virus and protects the genome from the environment and aids in attachment of virus to host cell. Some viruses are additionally enveloped, i.e. the capsid is coated with a lipid membrane also referred to as the viral envelope. The envelope is acquired by the capsid from an intracellular membrane of the host cell, such as from the inner nuclear membrane, the golgi membrane or the cell's outer membrane.

In a preferred embodiment of the method of the invention, the viruses are selected from the group consisting of influenza viruses, polio viruses, herpes simplex viruses-1, vaccinia viruses and adenoviruses.

Influenza viruses are part of the family of Orthomyxoviridae and belong to virus group V ((−)ssRNA). The three genera of influenza virus known—influenza virus A, B and C—are identified by antigenic differences in their nucleoprotein and matrix protein. Influenzavirus A infects humans, other mammals, and birds, and causes flu pandemics; influenzavirus B infects humans and seals and influenzavirus C infects humans and pigs.

Polio virus is the causative agent of poliomyelitis and is a human enterovirus of the family Picornaviridae. Poliovirus is composed of an RNA genome (Group IV ((+)ssRNA)) and a protein capsid. The genome is a single-stranded positive-sense RNA genome that is about 7500 nucleotides.

Herpes simplex virus 1 (HSV-1), also known as human herpes virus 1 (HHV-1), is a member of the herpes virus family, Herpesviridae, that infect humans and belongs to group I (dsDNA). HSV-1 produces cold sores and is ubiquitous and contagious.

Vaccinia virus (VACV or VV) is a large, complex, enveloped virus belonging to the poxvirus family. It has a linear, double-stranded DNA genome approximately 190 kbp in length, which encodes for ~250 genes. Vaccinia virus is best known for its role as a vaccine that eradicated the smallpox disease, making it the first human disease to be successfully eradicated by science.

Adenoviruses are medium-sized (90-100 nm), non-enveloped icosahedral viruses composed of a nucleocapsid and a double-stranded linear DNA genome (group I (dsDNA)). Adenoviruses are for example responsible for respiratory diseases, conjunctivitis as well as gastroenteritis. Adenoviruses are also used as vehicles to administer targeted therapy, for example in the form of recombinant DNA or protein.

In accordance with the present invention, the bacteria may be gram positive or gram negative bacteria.

In a preferred embodiment of the method of the invention, the bacteria are selected from the group consisting of *Bordetella pertussis, Clostridium tetani, Corynebacterium diphtheriae, Neisseria meningitidis, Streptococcus pneumoniae, Haemophilus influenza, Vibrio cholerae, Salmonella enterica* and *Bacillus anthracis*.

Unless otherwise defined, all technical and scientific terms used herein have the same meaning as commonly understood by one of ordinary skill in the art to which this invention belongs. In case of conflict, the patent specification, including definitions, will prevail.

The figures show:

FIG. 1: HSV-1 was stored at different storage conditions (RT, 4° C., −20° C., 37° C.) in the presence of or absence of the protecting solution of the invention for different amounts of time (0, 7, 14, 21, 28 days). Subsequently, HSV-1 was used for inoculation in cell culture and the virus titer was titrated.

Figure 2:
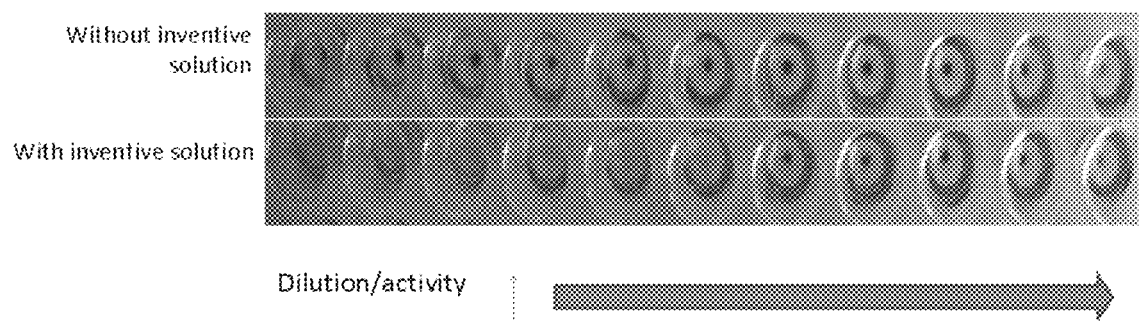

FIG. 2: The activity of influenza A is higher in virus preparations with the protecting procedure according to the present invention as indicated by lattice formation (no visible red button) even at high dilutions of virus.

Figure 3:
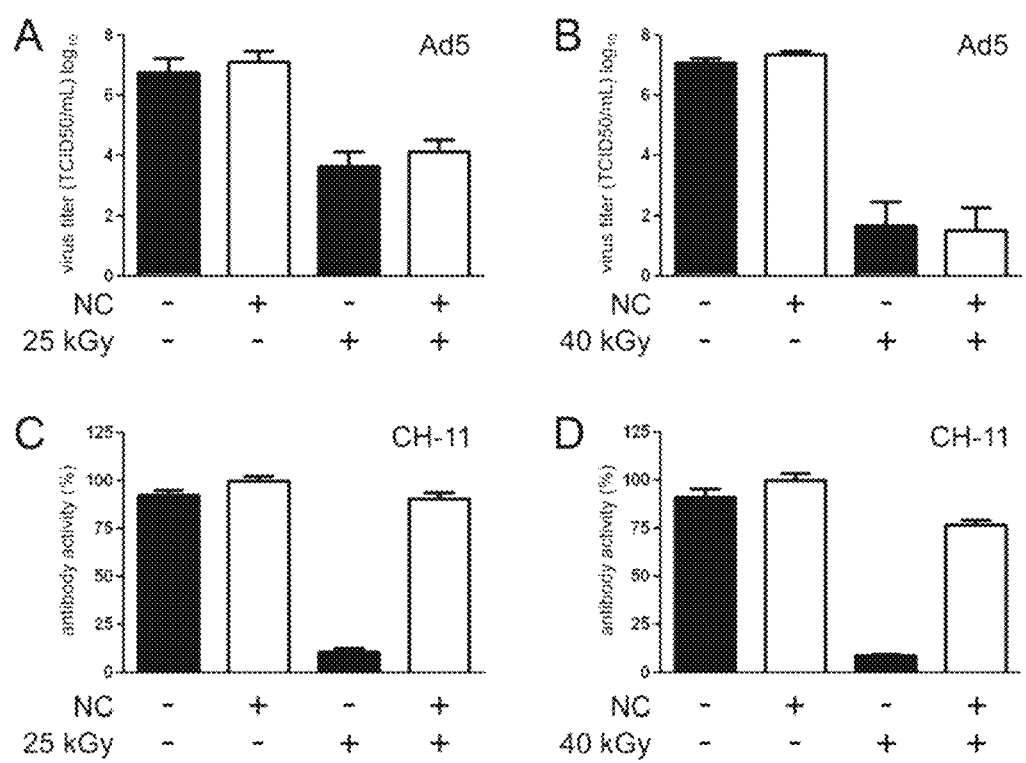

FIG. 3: Adenovirus type 5 (Ad5) infectivity assay. (A/B) Ad5 samples were β-irradiated at 25 kGy (A) and 40 kGy (B) with and without nano-coating. The titers of infective virus particles before and after irradiation are shown. (C/D) In the same setting an IgM antibody was irradiated. The relative antigen binding capacity before and after irradiation is shown.

Figure 4:
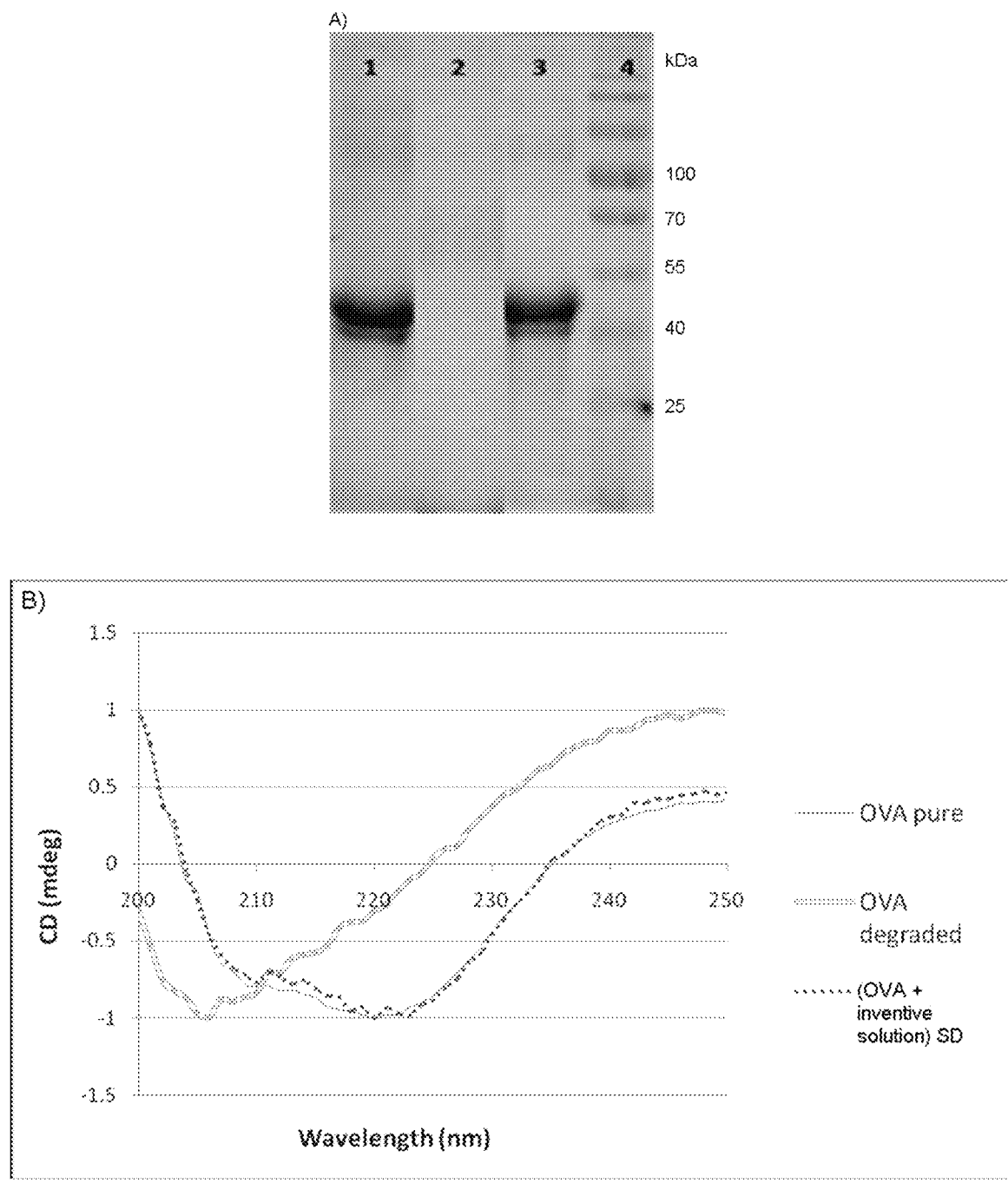

FIG. 4: (A) SDS-PAGE; Lane 1: OVA control, Lane 2: OVA degraded, Lane 3: (OVA+ inventive solution) SD, Lane 3: Marker (PAGERULER™ (prestained protein ladder)); (B) CD spectra of OVA control, OVA degraded and (OVA+ inventive solution) SD (spectra of protein only).

Figure 5:
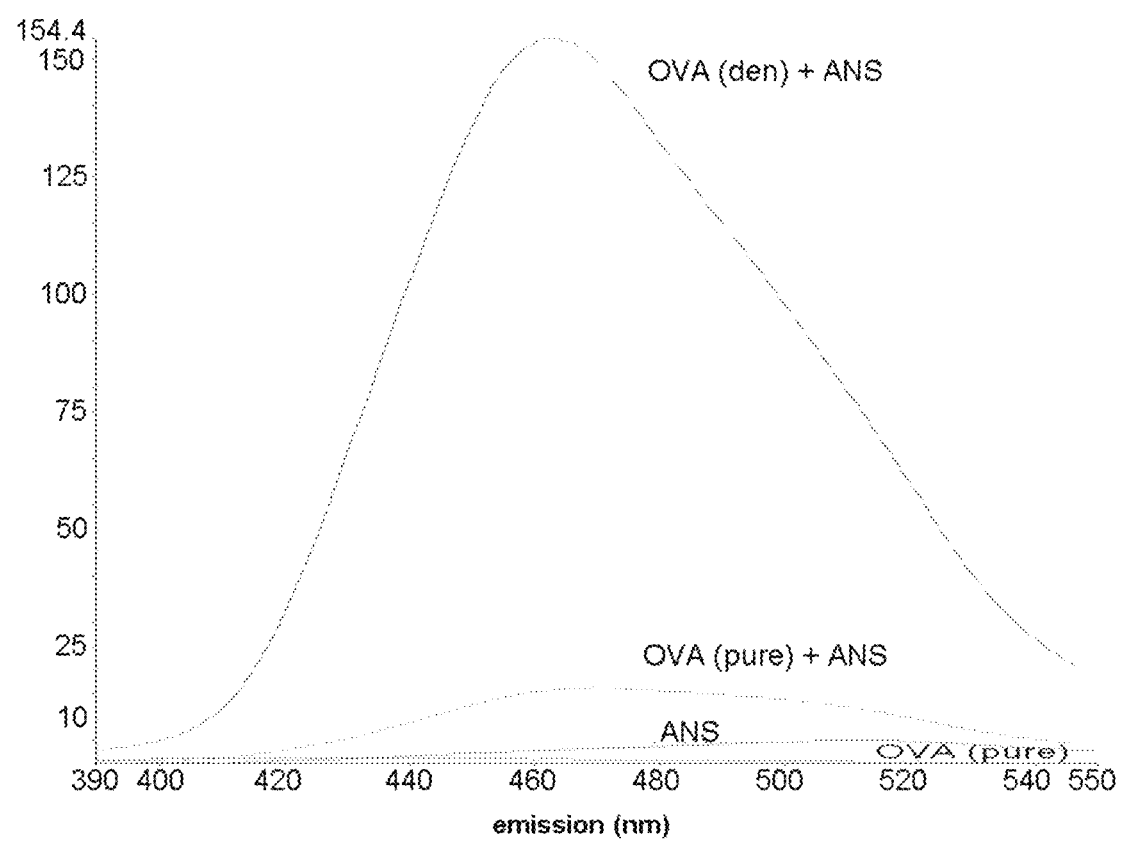

FIG. 5: Enhancement of fluorescence intensity of ANS on binding to OVA.

Figure 6:
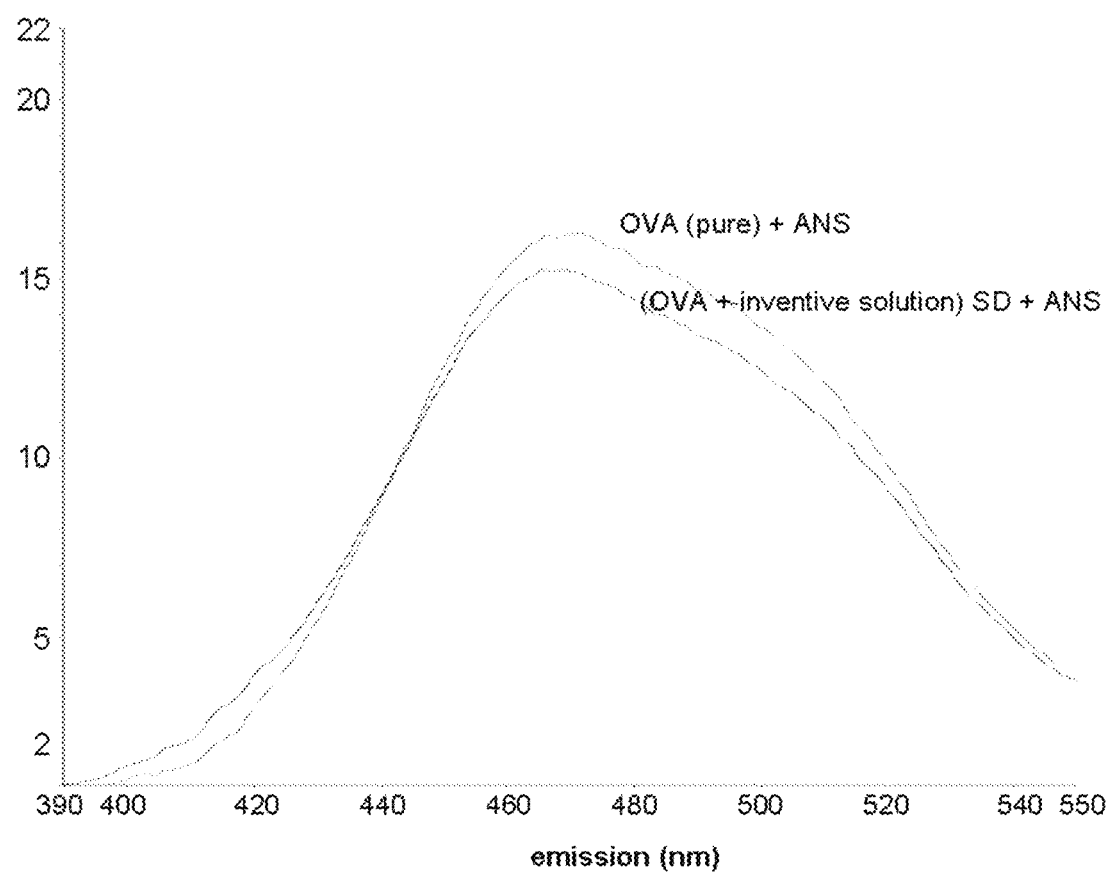

FIG. 6: Fluorescence intensity of OVA control and (OVA+ inventive solution) SD (spectra of protein only) after binding with ANS.

Figure 7:
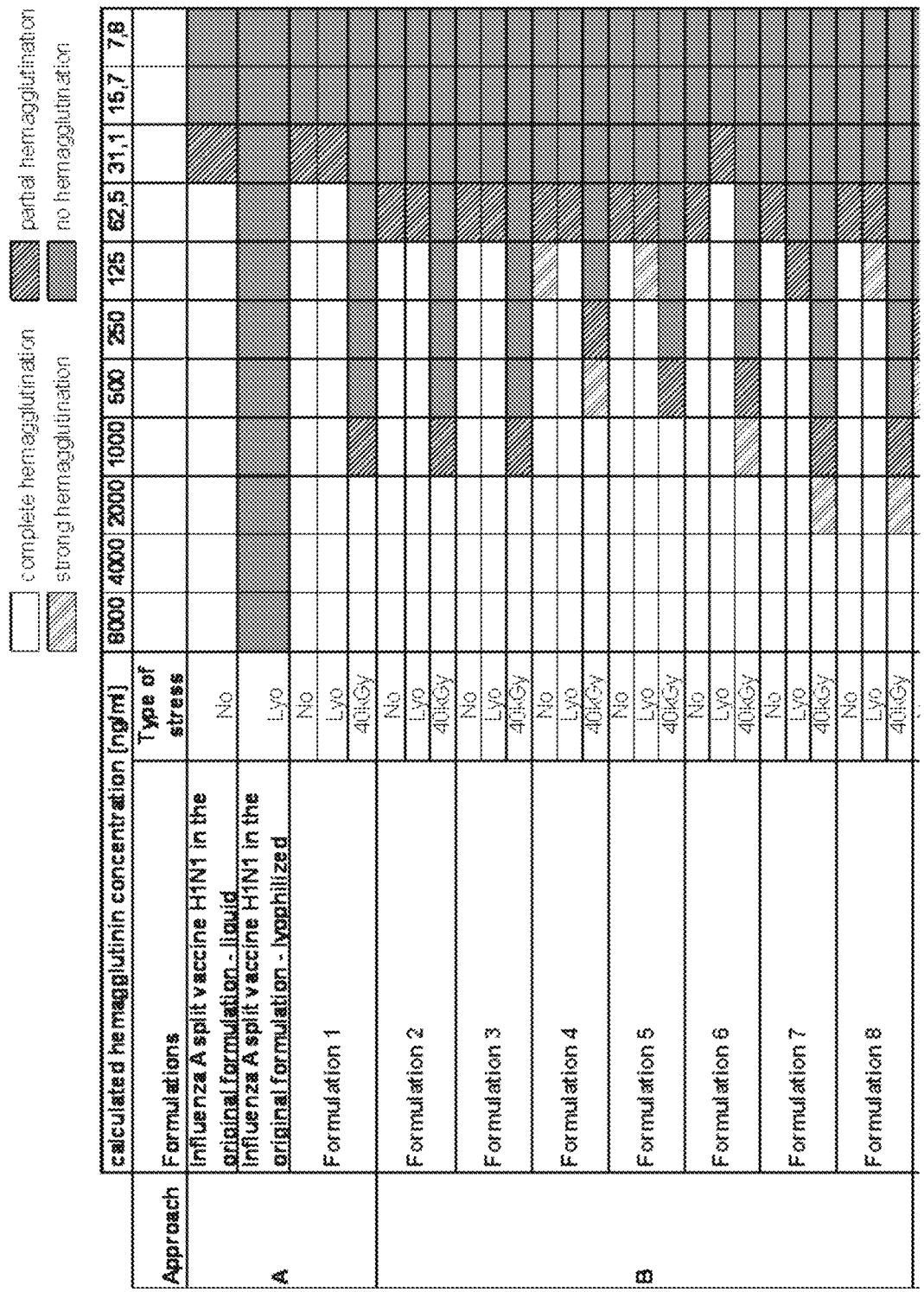
Figure 7:
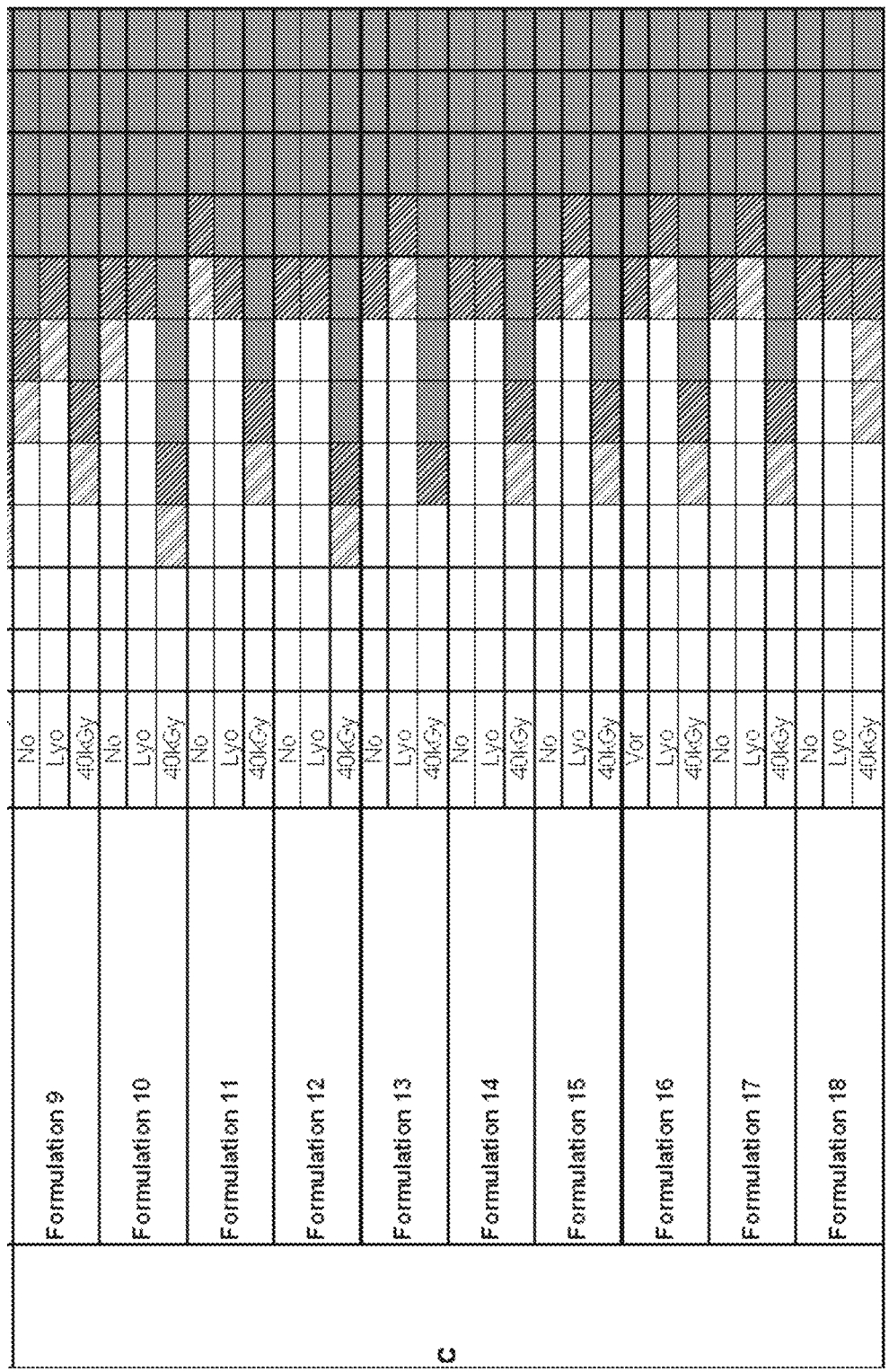

FIG. 7: Effects of different compositions on the functionality of hemagglutinine under stress conditions.

Activity of an inactivated influenza A H1N1 split vaccine, respective hemagglutination activity, formulated with different compositions of the protecting solution against different types of stresses like freeze drying and β irradiation with 40 kGy. Influenza A H1N1 split vaccine was rebuffered in compositions according to the present invention, containing seven amino acids (amino acid mixture 1: Ala, Arg, Gly, Glu, Lys, His, Trp) or five amino acids (amino acid mixture 2: Ala, Arg, Gly, Glu, Lys and amino acid mixture 3: Ala, Gly, Glu, His, Trp, respectively), supplemented with the dipeptide carnosin, other dipeptides and glycyrrhizic acid, respectively.

The examples illustrate the invention:

EXAMPLE 1

Testing of Infectivity after Liquid Storage

HSV-1 was propagated in cell culture. After determination of the virus titer by titration the virus was split into different samples for different storage conditions (RT, 4° C., −20° C., 37° C.) in the presence of or absence of protecting solution with and without glycyrrhizic acid. As a control, PBS was used. At different times (0, 7, 14, 21, 28 days) after experimental set-up HSV-1 was used for inoculation in cell culture and titration of the titer, accordingly. The maximum observation period was four weeks.

EXAMPLE 2

Influenza a HA Assay Showing Maintenance of Antigenicity

Inactivated influenza A virus was dialyzed at 2 to 8° C. versus the protecting solution according to the present invention. The w/w (virus/excipients of the protecting solution) ratio was between 1:10 and 1:100. Lyophilization was done in 100 μl volumes and lyophilisates were irradiated with 25 kGy β-irradiation. Additional data were obtained for a variety of different compositions of the protecting solution as shown in table 1. Furthermore, irradiation with 40 kGy β-irradiation was carried out as an alternative approach.

After irradiation and reconstitution, the functionality of the samples was evaluated in the hemagglutination assay (HA). As shown in FIG. 2, in contrast to the control, which showed a complete loss of antigenicity of influenza A in storage buffer, the hemagglutination activity was almost fully maintained after reconstitution of influenza A lyophilized in the inventive solution.

Table 1 provides an overview over the different compositions of the protecting solution of the present invention used in the example. Compositions with seven amino acids (amino acid mixture 1; Ala, Arg, Glu, Gly, Lys, His, Trp) or with five amino acids (amino acid mixture 2; Ala, Arg, Glu, Gly, Lys and amino acid mixture 3: Ala, Gly, Glu, His, Trp, respectively) were used. Compositions containing the dipeptide carnosine, glycyrrhicic acid, additional dipeptides, and combinations thereof, resulted in the best protection against lyophilisation-mediated and/or irradiation-mediated loss of functionality. The experiments revealed that the exclusion of amino acids that may have unappreciated side effects upon prolonged storage (e.g. oxidation sensitive; hygroscopic) resulted in reduced protection. When GA and/or carnosine, and/or dipeptides (Gly-Tyr; Gly-GLy; Gly-Gln) were supplemented to these compositions, the protecting effects of the composition could be increased. After the substitution of selected amino acids with dipeptides and/or GA the osmolarity of the composition is lower and may therefore be beneficial for therapeutical purposes.

TABLE 1

Compositions of the applied formulations 1 to 18

| | Amino acids | Supplements |
|---|---|---|
| Formulation 1 | Ala, Arg, Gly, Glu, Lys, His, Trp | |
| Formulation 2 | Ala, Gly, Glu, His, Trp | |
| Formulation 3 | Ala, Arg, Gly, Glu, Lys | Carnosin, N-acetyl-Trp |
| Formulation 4 | Ala, Arg, Gly, Glu, Lys, Trp | Carnosin, glycyrrhizic acid |
| Formulation 5 | Ala, Arg, Gly, Glu, Lys, His | N-acetyl-Trp, β-alanine |
| Formulation 6 | Ala, Arg, Gly, Glu, Lys | Carnosin, Gly-Tyr, N-acetyl-Trp, N-acetyl-His |
| Formulation 7 | Ala, Arg, Gly, Glu, Lys | Carnosin, Gly-Tyr, Gly-Gly, Gly-Gln |
| Formulation 8 | Ala, Arg, Gly, Glu, Lys | Gly-Tyr, Gly-Gly, Gly-Gln |
| Formulation 9 | Ala, Arg, Gly, Glu, Lys | N-acetyl-Trp, N-acetyl-His, β-alanine, glycyrrhizic acid |
| Formulation 10 | Ala, Arg, Gly, Glu, Lys | Carnosin, Gly-Tyr, glycyrrhizic acid |
| Formulation 11 | Ala, Arg, Gly, Glu, Lys | Gly-Tyr, Gly-Gly, glycyrrhizic acid |
| Formulation 12 | Ala, Arg, Gly, Glu, Lys | Gly-Gly, Gly-Gln, glycyrrhizic acid |
| Formulation 13 | Ala, Arg, Gly, Glu, Lys | Carnosin, Gly-Tyr, N-acetyl-Trp, N-acetyl-His, glycyrrhizic acid |
| Formulation 14 | Ala, Arg, Gly, Glu, Lys | Carnosin, Gly-Gly, N-acetyl-Trp, N-acetyl-His, glycyrrhizic acid |
| Formulation 15 | Ala, Arg, Gly, Glu, Lys | Carnosin, Gly-Gln, N-acetyl-Trp, N-acetyl-His, glycyrrhizic acid |
| Formulation 16 | Ala, Arg, Gly, Glu, Lys | Carnosin, Gly-Tyr, Gly-Gly, Gly-Gln, glycyrrhizic acid |
| Formulation 17 | Ala, Arg, Gly, Glu, Lys | Carnosin, N-acetyl-Trp, Gly-Tyr, Gly-Gly, Gly-Gln, glycyrrhizic acid |
| Formulation 18 | Ala, Arg, Gly, Glu, Lys | Gly-Tyr, Gly-Gly, Gly-Gln, glycyrrhizic acid |

EXAMPLE 3

Virus Irradiation and Maintenance of Antigenicity

Virus inactivation studies were performed using human adenovirus type 5 (Ad5). Specifically, 50 μL of virus suspension were dried at 37° C. on the bottom of sterile polystyrol tubes. The dried virus was then overlaid with 50 µL of the protecting solution and dried again at 37° C. After β-irradiation at 25 kGy or 40 kGy (controls were not irradiated), the virus/protective solution bilayer was resuspended in 1 mL of MEM, and the titer of infectious virus was determined by means of end-point titration (FIG. 3A/B). In parallel, the same experimental setup was employed with IgM (LO-MM-3; FIG. 3C/D).

We show that β-irradiation led to quantitative inactivation of Ad5 (25 kGy,≥99.9% reduction, 40 kGy ≥99.999% reduction; FIG. 3 A/B) while the functionality of an IgM antibody was maintained. These results demonstrate that the inventive solution selectively stabilizes and protects protein structures outside the virus while at the same time allowing inactivation of the infectivity.

EXAMPLE 4

Failure of Protecting Solution to Stabilize Living Eukaryotic Cells During Freezing and Thawing Cultured fibroblasts were harvested after reaching confluency in culture plates. Cells were counted and reconstituted with a) DMSO as a standard procedure or b) in protecting solution or c) in different mixtures of DMSO and protecting solution (SPS®) before freezing and storing in −80° C. After thawing, the viability of cells was analyzed by trypan blue and the ability to form new cultures in vitro. The results are shown in table 2 below.

The samples were reconstituted in (all in DMEM/20% FKS (v/v)):

1 10% DMSO (v/v)/0 (v/v) SPS (20 g/l)=negative control
2 7.5% DMSO (v/v)/2.5% (v/v) SPS (20 g/l)
3 5% DMSO (v/v)/5% (v/v) SPS (20 g/l)
4 2.5% DMSO (v/v)/7.5% (v/v) SPS (20 g/l)
5 0% DMSO (v/v)/10% (v/v) SPS (20 g/l)
6 0 DMSO (v/v)/0% (v/v) SPS (20 g/l)=positive control
Protecting solution with 20% FCS:
7 SPS 10 mg/ml+20% FKS/10% DMSO
8 SPS 10 mg/ml+20% FKS/0% DMSO

TABLE 2

Lack of stabilization of eurkayotic cells in the inventive solution

| | Cells/ml vital | Cells/ml dead | Total number of live cells | Vitality in % | Recovery in % (relative to amount of cells frozen) |
|---|---|---|---|---|---|
| 1 | $1.6 \times 10^5$ | — | $8.0 \times 10^5$ | 100 | 85.6 |
| 2 | $2.2 \times 10^5$ | $0.2 \times 10^5$ | $11.0 \times 10^5$ | 91.7 | 100 |
| 3 | $0.8 \times 10^5$ | $0.2 \times 10^5$ | $4.0 \times 10^5$ | 80 | 42.3 |
| 4 | $0.4 \times 10^5$ | $0.4 \times 10^5$ | $2.0 \times 10^5$ | 50 | 21.4 |
| 5 | — | $0.6 \times 10^5$ | — | 0 | — |
| 6 | — | $1.2 \times 10^5$ | — | 0 | — |
| 7 | $0.6 \times 10^5$ | — | $3.0 \times 10^5$ | 100 | 32.1 |
| 8 | — | $0.8 \times 10^5$ | — | 0 | — |

It was further tested how cells attached to the culture dish 24 hours after thawing. The level of attachment was determined microscopically. The results are summarized in table 3 below.

TABLE 3

Attachment to cell culture dishes 24 hours after thawing

| | Attachment |
|---|---|
| 1 | cells attach well, only a few individual loose cells |
| 2 | cells attach well, only a few individual loose cells |
| 3 | cells attach well, some individual loose cells or cell fragments |
| 4 | cells attach well, some individual loose cells or cell fragments |
| 5 | only loose cells or cell fragments |
| 6 | only loose cells or cell fragments |
| 7 | cells attach well but have a slightly round shape, only a few individual loose cells |
| 8 | only loose cells or cell fragments |

EXAMPLE 5

Material and Methods

Preparation of the Protecting Solution

The protecting solution employed in the examples above contains L-alanine, L-arginine, L-glutamic acid, glycine, L-histidine, L-lysine monohydrochloride and L-tryptophan.

The protective solution was prepared by specifically combining the different amino acids according to the present invention and, optionally, glycosidic excipients (here, glycyrrhizic acid) to reach a stock concentration of about 100 g/L. The weight:weight (w/w) ratio of the solid content of final solution (1-25 g/L) to the agents to be protected was >2:1. All components were non-toxic. Amino acids are approved for intravenous infusion (Fong and Grimley), Glycyrrhizic acid has been approved for intravenous application in the treatment of chronic hepatitis, and its safety has been well documented in several clinical studies. In the inventive solution, glycyrrhizic acid can be used in a range between 1-10000 µg/mL.

Virus Infectivity Assay

For the infectivity/inactivation study, adenovirus type 5, strain Adenoid 75 (American Type culture collection, ATCC-VR-5) was propagated on human lung cancer cell line A549 (ATTC-CCL-185). For virus propagation, cells were grown at 37° C. and 5% CO2 in minimum essential medium (MEM) supplemented with 5% fetal calf serum (FCS). The virus titer was determined by means of end-point titration (eight wells per dilution in a 96-well microtiter plate), with 50 µL virus dilution and 50 µL A549 cells ($10\text{-}15 \times 10^3$ cells) per well. For the experiments, a titer of $1.1 \times 10^9$ tissue culture infectious dose (TCID50)/mL was used. Specifically, a volume of 50 µL virus suspension was dried at 37° C. on the bottom of sterile polystyrol tubes. The dried virus was then overlaid by 50 µL of the protective solution (20 g/l) and dried again at 37° C. After β-irradiation at 25 kGy or 40 kGy (controls were not irradiated), the virus/protective solution bilayer was resuspended in 1 mL MEM. The virus titer was determined again as described above. The cultures were observed for cytopathic effects (CPE) after 7 days of inoculation.

Virus controls were treated identically but without β-irradiation. The virus titers are expressed as TCID50/mL including standard deviation. Titer reduction is expressed as the difference between the virus titer after β-irradiation and control virus titer.

Statistics

All experiments were done at least five times. Where relevant, data are presented as mean+/− SEM. Statistical analyses were performed by Student's t-Test (GraphPad

EXAMPLE 6

Stabilization of Ovalbumin During Spray Drying

Ovalbumin, a model antigen commonly employed in immunization, was used as a proof-of-principle to confirm the usefulness of the inventive solution for the stabilization of antigens during spray drying. The dried powder was then characterized for integrity using Circular dichroism (CD), Sodium dodecyl sulphate polyacrylamide gel electrophoresis (SDS-PAGE) and fluorescence spectroscopy.

Materials and Methods

Ovalbumin was purchased from Sigma (St. Louis, Mo., USA). The inventive solution was as described above (see embedding solution). 1-Anilino-8-naphthalene sulfonate (ANS) was also purchased from Sigma (St. Louis, Mo., USA). All other reagents were of analytical grades.

Preparation of Spray-Dried Protein

3% (w/v) of Ovalbumin along with 6% (w/v) of the inventive solution were spray dried using a Büchi B-290 laboratory spray dryer (Büchi, Flawil, Switzerland). Inlet air temperature was set to 120° C., the air flow was 470 L/h, the pump rate was 7.5 ml/min and the outlet air temperature was between 50-55° C.

SDS-PAGE

SDS-PAGE was carried out using a Bio-Rad MINI-PROTEAN® 3 gel electrophoresis system (Bio-Rad Laboratories, Hercules, USA). 10 µl of protein samples (0.5 mg/ml) was loaded into each well after incubating (95° C., 5 min) with 10 µl of sample buffer and subjected to electrophoresis at voltage of 200 V for about 55 min. The proteins were visualised with Coomassie blue staining.

Circular Dichroism (CD)

Jasco J-715 spectropolarimeter (JASCO International Co. Ltd, Hachioji city, Japan) was used to assess the secondary structure of proteins after spray drying. CD spectra were recorded in far UV range (200 to 250 nm) region with a sampling interval of 1.0 nm in a 0.05 cm path length cuvette. The solution of the invention was separated from the protein using an ultra-filtration device (VIVASPIN® 6 from Sartorius Stedim biotech, Gottingen, Germany) since it has some signal in CD. All spectra are average of two scans and were background corrected and normalised. Spectra were then compared to that of pure/unprocessed protein.

Fluorescence Spectroscopy

The fluorescence spectra were recorded in a fluorescence spectrometer (LS55 from PerkinElmer, Waltham, USA) using a 1 cm path length cuvette. Intrinsic fluorescence of ANS was measured by exciting it at 360 nm and the emission spectrum was recorded in 390-550 nm range. Fluorescence spectra were corrected for the background spectrum of solvent.

Results

SDS-PAGE analysis of OVA control and spray dried OVA with the inventive solution is shown in FIG. 4(A). The same gel pattern is observed in both samples and no low molecular weight bands are present, indicating that no degradation of the OVA molecule has taken place upon spray drying.

In addition, as shown in FIG. 4(B), the CD spectra of OVA after spray drying with the inventive solution resembles the OVA control indicating that no change in secondary structure can be observed after re-dispersion.

1-Anilino-8-naphthalene sulfonate (ANS) is practically non-fluorescent in water, but shows fluorescence upon binding to hydrophobic sites that exists on proteins. Accordingly, this fluorescence is greatly increased when the protein is denatured and thus serves as a measure of the degree of denaturation (FIG. 5). This phenomenon was used to characterise the integrity of OVA after spray drying. As seen in FIG. 6, the control and spray dried OVA with the inventive solution possess the same fluorescence intensity indicating that no denaturation event had taken place during spray drying.

In conclusion, the inventive solution is suitable for preserving the secondary structure during spray drying of Ovalbumin.

The invention claimed is:

1. A method for stabilizing viruses or bacteria, the method comprising:
   (a) embedding the viruses or bacteria in an aqueous solution, wherein the aqueous solution comprises:
      at least three different amino acids selected from at least three different groups of
         (i) amino acids with non-polar, aliphatic R groups;
         (ii) amino acids with polar, uncharged R groups;
         (iii) amino acids with positively charged R groups;
         (iv) amino acids with negatively charged R groups; and
         (v) amino acids with aromatic R groups;
      and wherein the aqueous solution is free or substantially free of sugar(s), silanes and protein(s),
   (b) storing the embedded viruses or bacteria in the aqueous solution for at least 7 days,
   wherein the viruses are whole viruses which maintain their infectivity and/or the ability to replicate after being embedded and stored in the aqueous solution for at least 7 days.

2. The method of claim 1, wherein the solution comprises at least one amino acid selected from each group of
   (1) an amino acid with non polar, aliphatic R groups;
   (2) an amino acid with polar, uncharged R groups;
   (3) an amino acid with positively charged R groups;
   (4) an amino acid with negatively charged R groups; and
   (5) an amino acid with aromatic R groups.

3. The method according to claim 1, wherein the solution comprises at least the amino acids selected from the groups of:
   (1) alanine, glutamate, lysine, threonine and tryptophan;
   (2) aspartate, arginine, phenylalanine, serine and valine;
   (3) proline, serine, asparagine, aspartate, threonine, and phenylalanine;
   (4) tyrosine, isoleucine, leucine, threonine, and valine;
   (5) arginine, glycine, histidine, alanine, glutamate, lysine, and tryptophan; and
   (6) alanine, arginine, glycine, glutamate, and lysine.

4. The method according to claim 1, wherein one or more of the amino acids are selected from the group consisting of natural non-proteinogenic amino acids and synthetic amino acids.

5. The method according to claim 1, wherein the solution further comprises an amphiphilic molecule.

6. The method according to claim 5, wherein the amphiphilic molecule is selected from the group consisting of a saponin or a fatty acid or derivatives thereof.

7. The method of claim 6, wherein the saponin is glycyrrhizic acid or a derivative thereof.

8. The method of claim 6, wherein the fatty acid is selected from the group consisting of short chain and medium chain fatty acids.

9. The method according to claim 1, wherein the w/w ratio between the excipients of the solution and the virus or bacteria is between 1:1 and 500:1.

10. The method of claim 1, further comprising the step of subsequently storing the stabilized viruses or bacteria at a temperature selected from about −90° C. to about 45° C.

11. The method of claim 1, wherein the stabilized viruses or bacteria are supplied for storage as a liquid preparation.

12. The method of claim 1, wherein the stabilized viruses or bacteria are supplied for storage as a dried preparation.

13. The method of claim 1, further comprising a subsequent inactivation step.

14. The method of claim 1, wherein the viruses are selected from the group consisting of influenza viruses, polio viruses, herpes simplex viruses-1, vaccinia viruses and adenoviruses.

15. The method of claim 1, wherein the bacteria are selected from the group consisting of pertussis, tetanus, diphtheria, meningococcus, pneumococcus, *Haemophilus influenza*, cholera, typhoid and anthrax.

16. The method of claim 1, wherein the aqueous solution further comprises at least one dipeptide of (ii) selected from the group consisting of carnosin, glycyltyrosine, glycylglycine and glycylglutamine.

17. The method of claim 12, further comprising irradiating the solution.

18. A method for stabilizing viruses or bacteria, the method comprising:
 (a) embedding the viruses or bacteria in an aqueous solution, wherein the aqueous solution comprises:
  at least three different non-peptidic independent amino acids selected from at least three different groups of
   (i) amino acids with non-polar, aliphatic R groups;
   (ii) amino acids with polar, uncharged R groups;
   (iii) amino acids with positively charged R groups;
   (iv) amino acids with negatively charged R groups; and
   (v) amino acids with aromatic R groups;
  and wherein the aqueous solution is free or substantially free of sugar(s), silanes and protein(s),
 (b) storing the embedded viruses or bacteria in the aqueous solution for at least 7 days,
 wherein the viruses are whole viruses which maintain their infectivity and/or the ability to replicate after being embedded and stored in the aqueous solution for at least 7 days.

* * * * *